United States Patent [19]
Chiang et al.

[11] Patent Number: 5,507,795
[45] Date of Patent: Apr. 16, 1996

[54] CATHETER WITH PERFUSION SYSTEM

[75] Inventors: Andrew L. Chiang, Fremont; Jeffrey W. Krier, El Granada; Ron R. Hundertmark, San Mateo; Robert T. Chang, Belmont; Grace Y. Schulz, San Carlos, all of Calif.

[73] Assignee: Devices for Vascular Intervention, Inc., Redwood City, Calif.

[21] Appl. No.: 236,485

[22] Filed: Apr. 29, 1994

[51] Int. Cl.⁶ .......................... A61B 17/32; A61B 17/14
[52] U.S. Cl. ................................ 606/167; 606/180
[58] Field of Search ..................... 606/79, 80, 86, 606/87, 88, 159, 167–169, 170–173, 180–181

[56] References Cited

U.S. PATENT DOCUMENTS

| | | | |
|---|---|---|---|
| 4,705,038 | 11/1987 | Sjostrom | 606/180 |
| 4,771,774 | 9/1988 | Simpson | 606/180 |
| 4,781,186 | 11/1988 | Simpson | 604/22 |
| 5,019,088 | 5/1991 | Farr | 606/180 |
| 5,026,384 | 6/1991 | Farr | 606/180 |
| 5,102,415 | 4/1992 | Guenther | 606/159 |
| 5,181,920 | 1/1993 | Mueller | 606/180 |
| 5,217,474 | 6/1993 | Zacca | 606/180 |
| 5,217,479 | 6/1993 | Shuler | 606/180 |
| 5,358,509 | 10/1994 | Fine | 606/180 |

*Primary Examiner*—Michael A. Brown
*Attorney, Agent, or Firm*—Douglas A. Chaikin

[57] ABSTRACT

Improved atherectomy catheters and methods of use are disclosed. The catheter includes a flexible body with a longitudinal passage therethrough. A housing is mounted at the distal end, with an elongated aperture formed in a lateral side. A drive cable is disposed in the passage of the catheter body, and a working element is disposed in the housing, attached to the distal end of the drive cable. Passages and openings are provided for flowing blood into the housing and for flowing blood from a proximal to a distal side of the cutting blade. An impeller can be provided proximal to the cutting blade to impel blood into the housing and past the blade. Blood flows through the housing and past the blade so as to perfuse tissue downstream from the device.

32 Claims, 7 Drawing Sheets

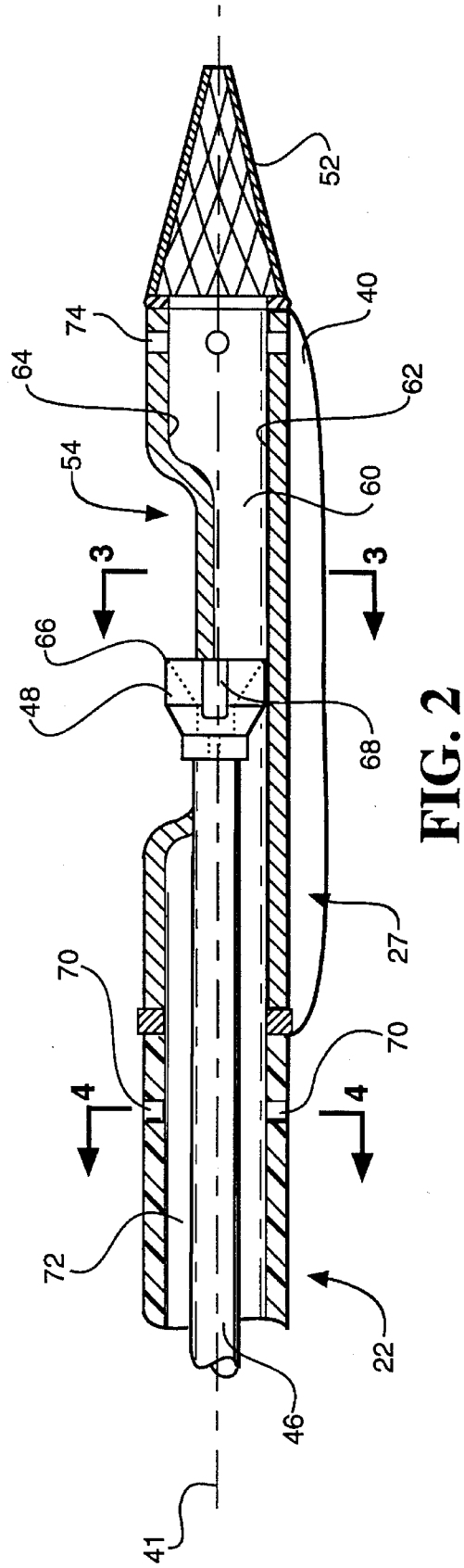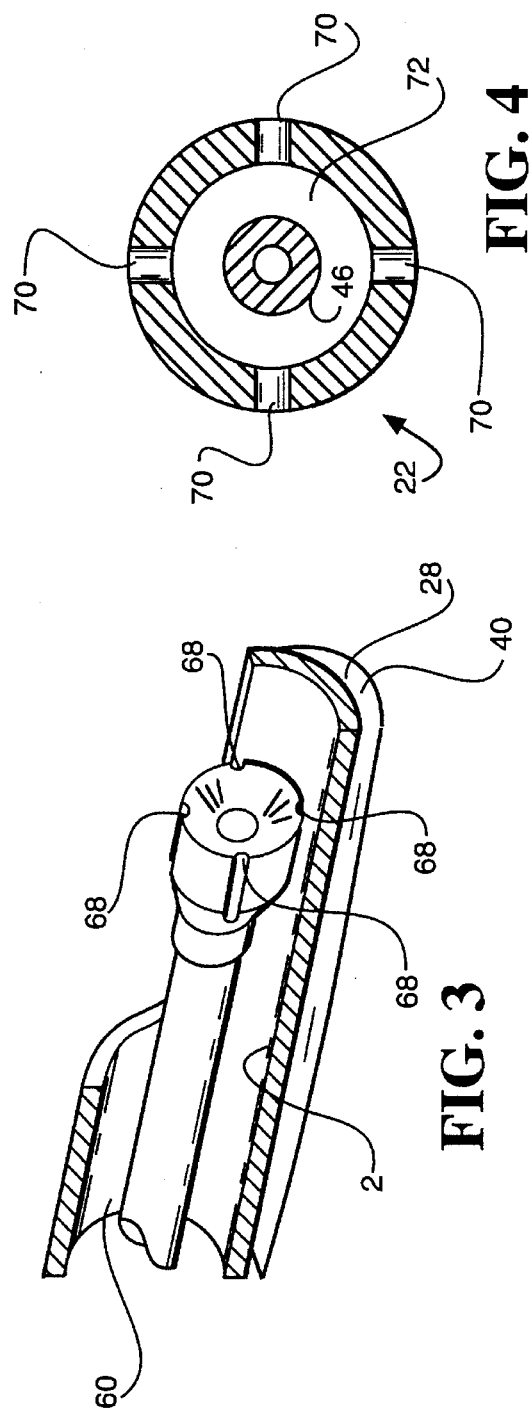

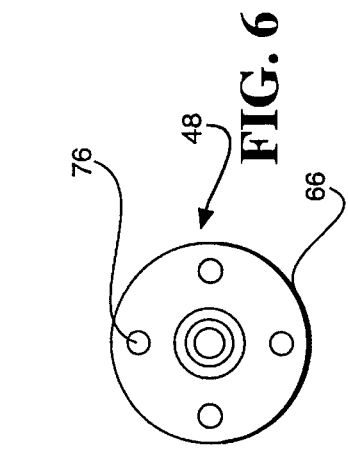
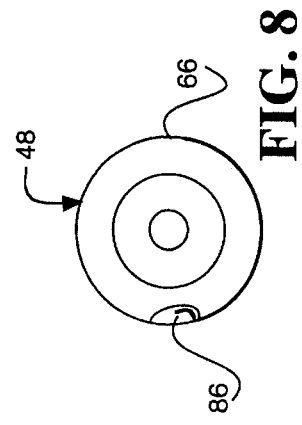
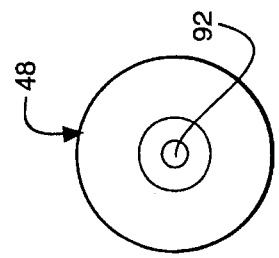
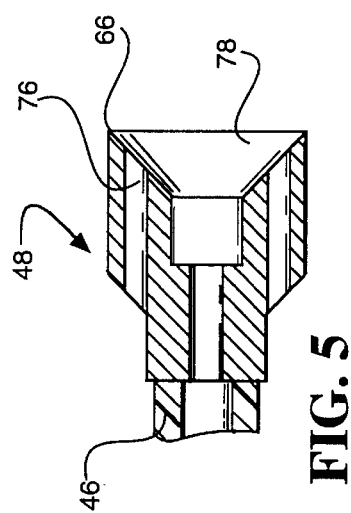
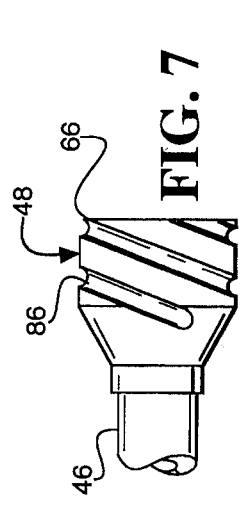
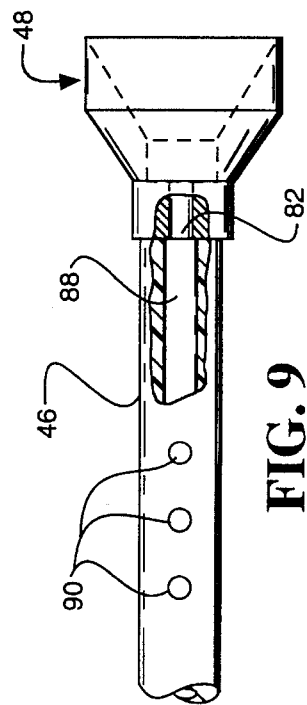

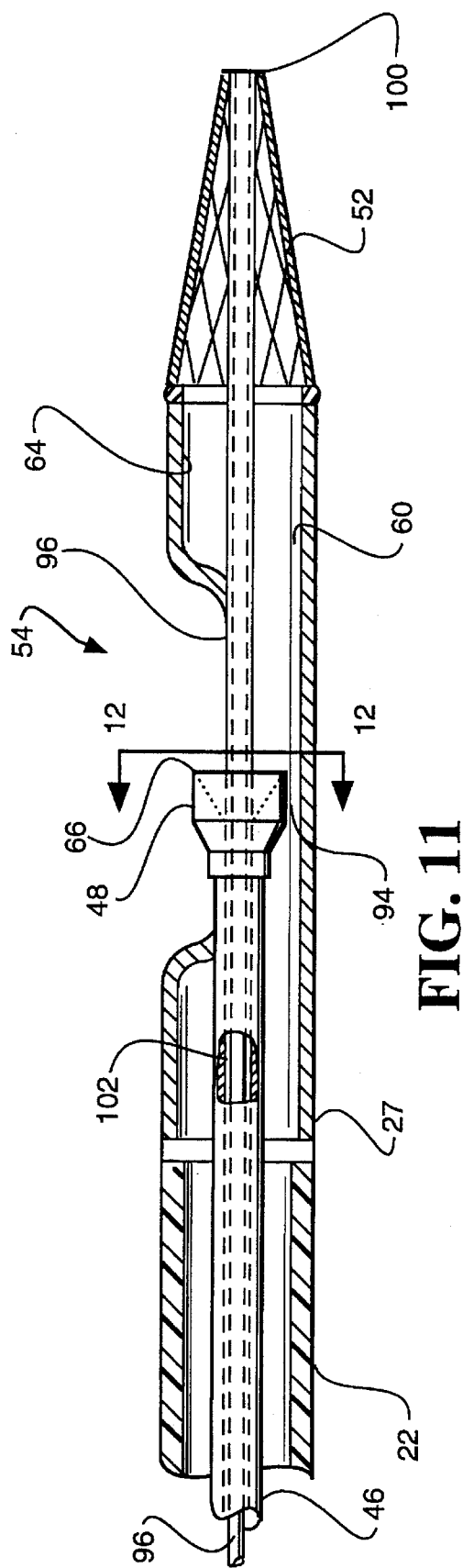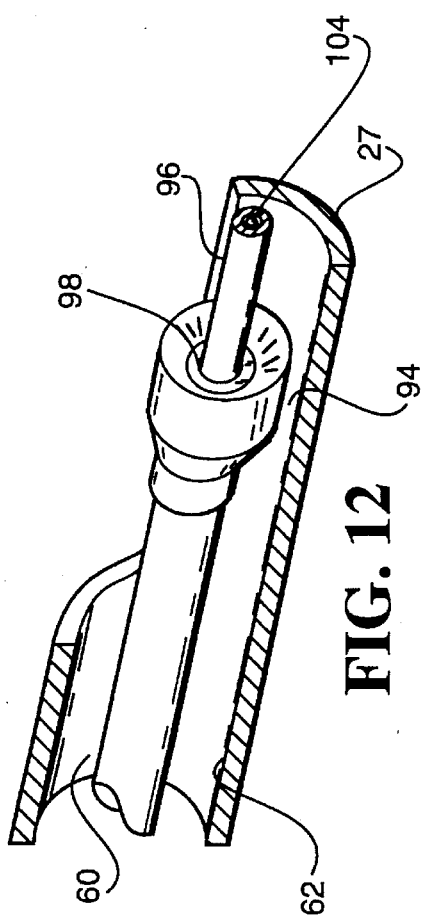
FIG. 11
FIG. 12

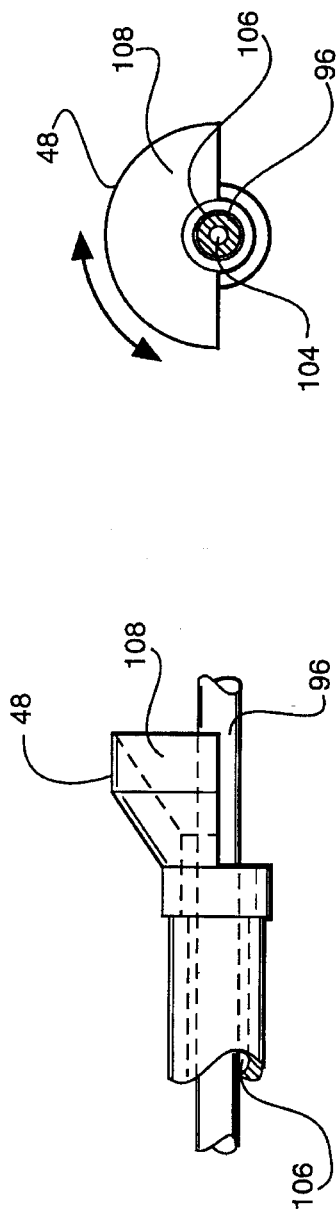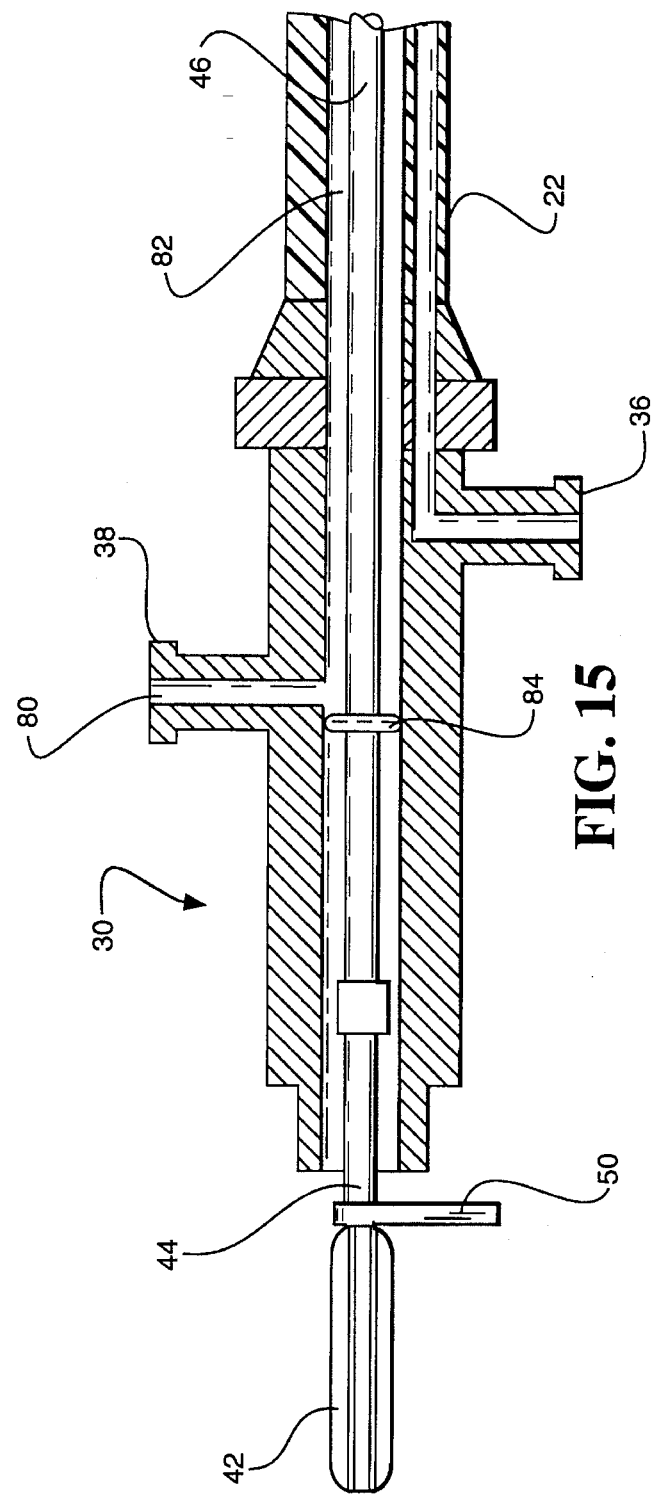

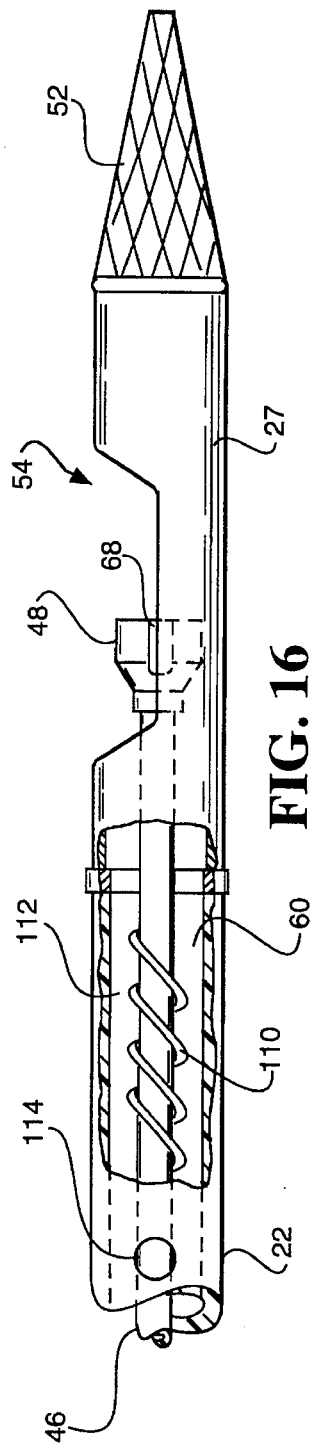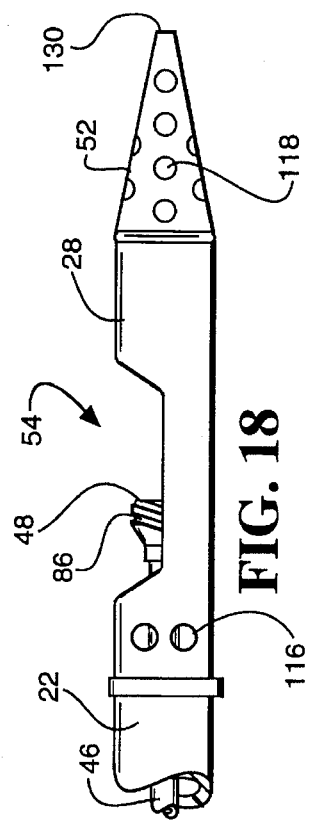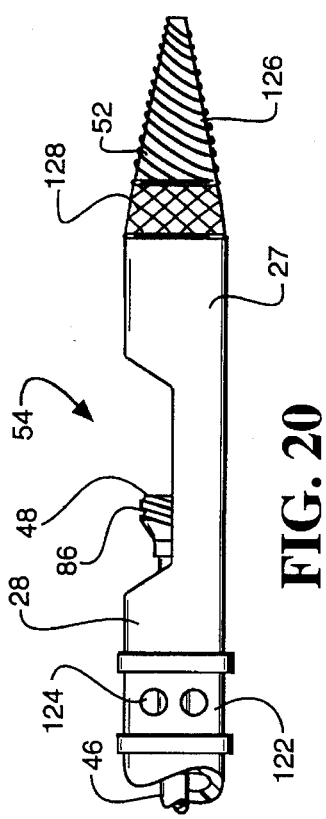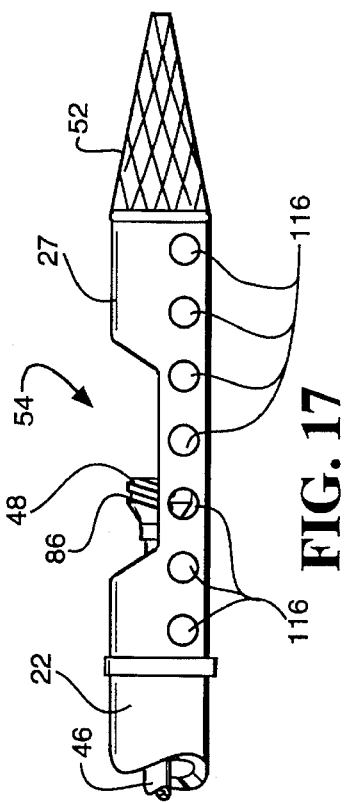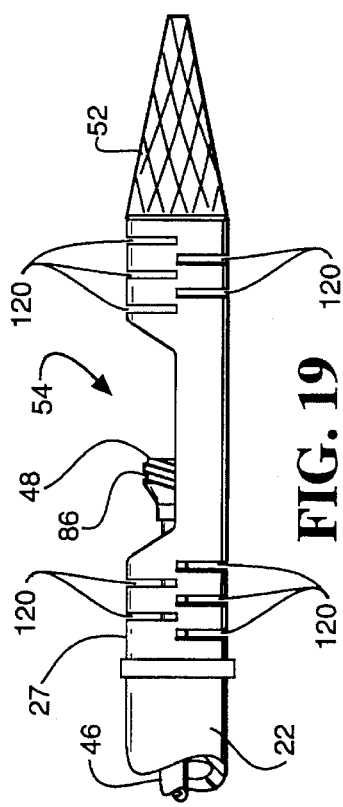

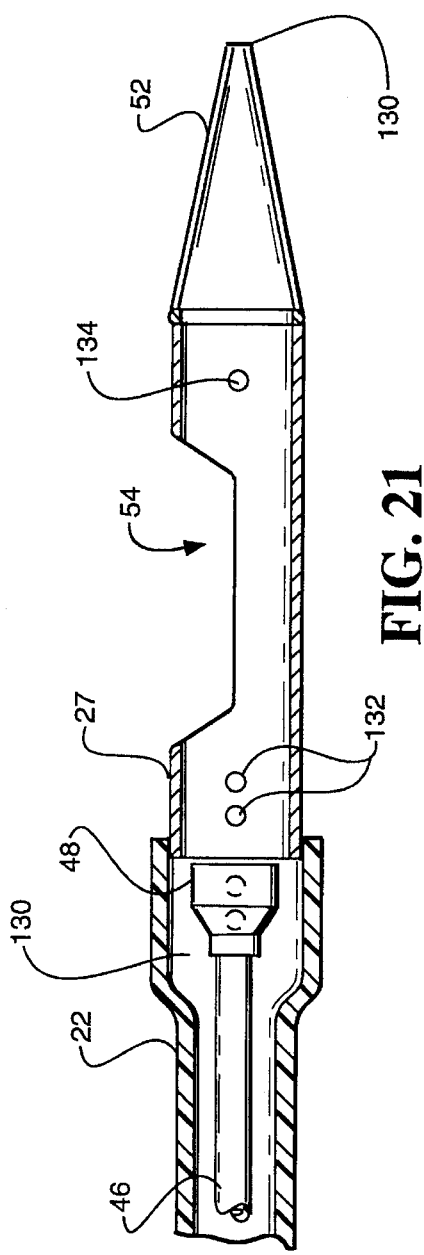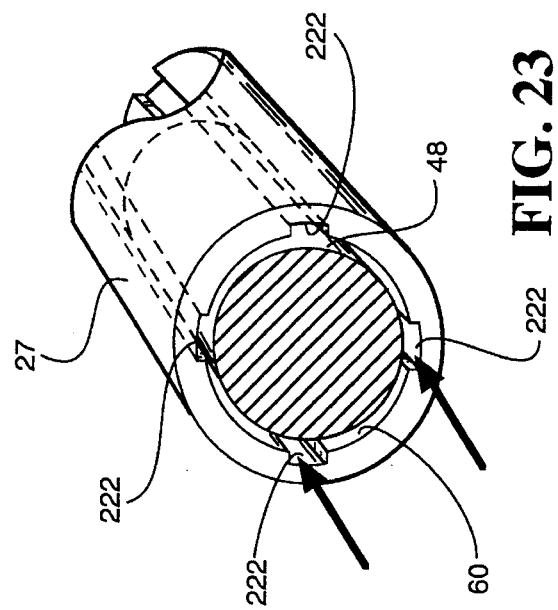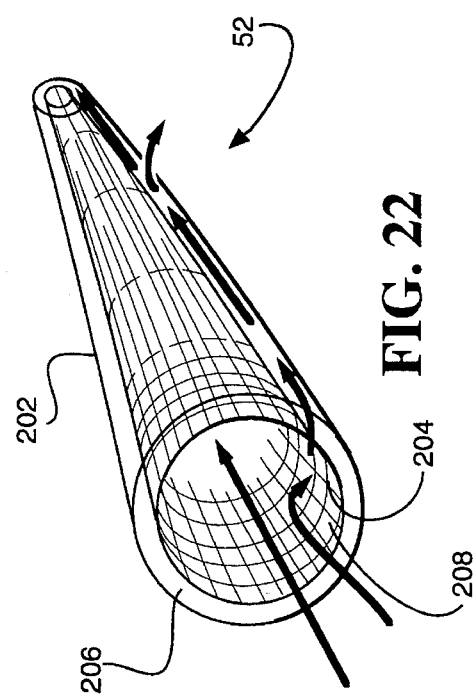

CATHETER WITH PERFUSION SYSTEM

RELATED APPLICATIONS

This application contains subject matter related to that in the following applications U.S. Ser. No. 08/357,999 (Attorney Docket No. DEVI1476); U.S. Ser. No. 08/363,142 (Attorney Docket No. DEVI1456); and U.S. Ser. No. 08/224,169 (Attorney Docket No. DEVI1467). The full disclosure of each of these applications is incorporated herein by reference.

1. Field of Invention

The present invention relates generally to the construction and use of vascular and other catheters. More particularly, the invention relates to intravascular catheters having a distal housing and an axially translatable work element therein.

2. Background of the Invention

Arteriosclerosis, also known as atherosclerosis, is a common human ailment arising from the deposition of fat-like substances, referred to as atheroma or plaque, on the walls of blood vessels. Such deposits occur both in peripheral blood vessels that feed the limbs of the body and in coronary blood vessels which feed the heart. When deposits accumulate in localized regions of a blood vessel, the regions become stenosed, blood flow is restricted and the person's health is at serious risk.

Numerous approaches for reducing and removing such stenotic deposits have been proposed, including balloon angioplasty, where a balloon-tipped catheter is used to dilate the stenosed region, atherectomy, where a blade or other cutting element is used to sever and remove stenotic material and laser angioplasty, where laser energy is used to ablate at least a portion of the stenotic material.

U.S. Pat. No. 5,163,910 describes a perfusion pump apparatus in an angioplasty balloon catheter Atherectomy catheters are described in U.S. Pat. Nos. 7,781,186; 4,926,858; 4,979,951; 5,047,040; 5,084,010; and Re. 33,569. Of these, the 4,979,951 and Re. 33,569 patents describe catheters having distal housing where a rotatable cutting blade receives a coaxial movable guidewire. The 7,781,186 patent describes atherectomy catheters having a flexible distal housing. Co-pending application Ser. No. 07/823,905, assigned to the assignee of the present application, describes an atherectomy catheter having a flexible nose cone attached to the distal end of a cutter housing. Co-pending application Ser. No. 07/971,697, assigned to the assignee of the present application, describes atherectomy catheters having helical cutting blades and/or blade guides.

Of particular interest to the present invention are atherectomy catheters and methods where a cutting blade is advanced past an opening in a housing at the distal end of a vascular catheter. By positioning the housing so that at least a portion of the stenotic material passes through the opening, the stenotic material can be severed and translated forwardly by advancing the cutting blade. Typically, such cutting blades are circular and are advanced while being rotated to effect the desired cutting.

Although such atherectomy catheters have enjoyed widespread success in both peripheral and coronary applications, one drawback associated with such catheters is the partial or total blockage of the vessel lumen caused by the presence of the catheter in the vessel. Atherectomy catheters occlude much of the vessel lumen during positioning and use, particularly in the narrower stenosed region of the vessel. Even where the housing does not completely occupy the vessel lumen, atherectomy catheters frequently employ an expandable balloon mounted to the housing to position the housing against the region of stenosis on the vessel wall and to cause the stenotic material to penetrate the opening in the housing. In such a case, the expanded balloon and housing together may block the vessel. Such occlusion of the vessel can cause an ischemic reaction in the patient resulting from insufficient blood flow to tissue downstream of the catheter.

While physicians experienced in using atherectomy catheters are generally capable of positioning the catheter and completing an atherectomy procedure at a particular treatment site before the onset of ischemia, less experienced users of such catheters, particularly those undergoing training in atherectomy procedures, take more time in positioning the catheter and completing the atherectomy. Moreover, in certain situations, the atherectomy procedure requires multiple passes of the cutter or otherwise take more time to remove the stenotic material from the treatment site. In such cases, blood flow through the vessel is reduced or stopped for such a time that there is an undesirably high risk of producing an ischemic reaction in the patient.

Balloon catheters for angioplasty treatment, in contrast to atherectomy catheters, are positioned in an artery with the balloon at the distal tip of the catheter in a deflated condition, allowing blood to flow around the catheter body and the balloon during positioning. The stenosed region is then dilated by inflating the balloon, which severely obstructs the vessel lumen. To prevent the onset of ischemia, various types of perfusion balloon catheters have been designed which allow blood to bypass the treatment site when the balloon is in the inflated state. Such perfusion balloon catheters typically have one or more apertures in the catheter body proximal to the balloon and one or more apertures distal to the balloon, with a passage through the catheter connecting the upstream and downstream apertures. Such catheters are described in U.S. Pat. No. 5,163,910, the complete disclosure of which is incorporated herein by reference.

The techniques for providing blood bypass in balloon angioplasty catheters have not been successfully adapted for use in known atherectomy catheters. This is due in large part to the cylindrical cutters typically used in atherectomy catheters. The diameter of these cutters is usually maximized for a given vessel size in order to sever as much of the stenotic tissue as possible in each pass of the cutter across the opening in the housing. Such catheters, therefore, block any portion of the vessel lumen not already blocked by stenosis, the housing, or the inflated balloon. Moreover, the cylindrical cutters usually have solid, unperforated walls and a closed proximal end so as to retain severed stenotic material within the open interior of the cutter. Thus, even if blood bypass apertures were formed in the catheter upstream of the housing, with a passage in the catheter to provide blood flow distally from the apertures as in perfusion balloon catheters, blood could flow only as far as the proximal side of the cutter, which would prevent further flow through or around the housing.

For these reasons, it would be desirable to provide improved designs for atherectomy and other catheters having a work element within a distal housing, operable through a side aperture in the housing. In particular, it would be desirable to provide atherectomy catheters having means for flowing blood through the housing of the catheter. In this manner, the tissue downstream of the catheter is perfused while the catheter is blocking the vessel lumen. Preferably, the desired catheter includes a perfusion system which will be adaptable to various types of work elements and, particularly, to rotating and reciprocating blades designed to sever stenotic material through the aperture in the housing. Desirably, the perfusion system for flowing blood through the housing should be effective both when the work element is in use, as well as when the work element is in an idle state and the catheter remains positioned in the vessel. It is also desirable for the perfusion system to positively impel blood from one side of the work element to the other side. Additionally, it is desirable for the perfusion system to minimize the cross-sectional area of the catheter and housing. The perfusion system should be compatible with various types of atherectomy catheters, including those with flexible or rigid housings as well as those having fixed or movable guidewires.

SUMMARY OF THE INVENTION

It is an object of this invention to provide a catheter having a perfusion system which allows blood to flow within the catheterized blood vessel, past the catheter in order to perfuse tissue downstream of the catheter.

It is another object of this invention to provide a catheter having a perfusion system as set forth above wherein various types of work elements are adapted to fit within the catheter housing.

It is yet another object of this invention to provide a catheter perfusion system as set forth above wherein blood is impelled through the catheter and beyond the work element with the catheter housing.

In accordance with these and other objects which will become apparent, the catheter having a perfusion system in accordance with this invention comprises:

- a catheter body having a distal end, a proximal end and a lumen therebetween;
- a housing having a longitudinal axis, a hollow interior, a proximal end affixed to the distal end, a perfusion port entry, a perfusion port exit, of the catheter body, a distal end, and an aperture on a lateral side of the housing;
- a work element disposed in the housing;
- a work element connector with a proximal end and a distal end, the connector disposed in the catheter body with the distal end affixed to the work element the perfusion port entry being proximal the work element, the perfusion port exit being distal the work element; and the housing defines;
- at least one passage the passage being in fluid communication with each perfusion port to facilitate perfusion of fluid through the housing and past the work element.

In one embodiment, the work element is a rotatable blade with a hollow interior, an open distal end and a proximal end. The work element connector is a drive cable, and the proximal end of the cutter is connected to the distal end of a drive cable disposed in a longitudinal lumen of the catheter body. The drive cable has a proximal end for coupling to a motor drive unit.

In another embodiment, the perfusion system includes at least one slot in an outer surface of the cutting blade extending from the proximal end to the distal end of the blade. Alternatively, the slots can be parallel to the longitudinal axis or the slots can be helical around the blade and configured to impel blood distally as the blade rotates.

In another embodiment the work element is a rotationally reciprocating blade, wherein the cutting portion of the blade is exposed through the aperture in the housing and the portion of the blade that remains in contact with the interior wall of the housing is slotted.

In another embodiment, the blade contains at least one tunnel extending through an internal portion of the blade from the proximal end to the distal end thereof.

In another embodiment, the cutting blade has a cross-sectional area in the range of 75% to 98% of the cross-sectional area of the interior of the housing, thereby creating an annular passage between the cutting blade and the housing.

In a preferred embodiment, the catheter body or the housing includes one or more openings for permitting blood to flow into the housing proximal to the cutter. In various embodiments the openings are various shapes including round holes, rectangular slots and other shapes.

In another embodiment, the drive cable has an axial passage and at least one inlet hole near its distal end in communication with the axial passage. The blade has a passage with a proximal end in communication with the axial passage in the drive cable and a distal end thereof, wherein bypass flow occurs through the axial passage and the blade passage. In one embodiment, the axial passage is configured to receive a movable guidewire and is sized so that blood flows through the passage around the guidewire and through an axial bore in the cutting blade.

In another embodiment, a distal portion of the catheter body, or a proximal portion of the housing comprises a receiving space configured to receive at least a portion of the cutting blade. Side holes are provided in the housing or the distal portion of the catheter body. The cutting blade is retracted to a point proximal to the side holes, so that blood enters the side holes and flow through the housing to perfuse tissue downstream from the device.

In another embodiment, the catheter includes an impelling blade attached to the drive cable proximal to the cutting blade for impelling blood distally. Rotation of the drive cable rotates the impeller blade to pump blood distally into the housing. Usually, openings are provided in the catheter body near the impeller blade so that blood is drawn into the catheter body and forced distally by the impeller blade into the housing. In a preferred embodiment, the impeller blade is helical. In other embodiments the blade has a variety of configurations, including a propeller, a radial blade or other configuration.

In another embodiment, the catheter includes at least one outlet through which blood flows out of the housing. Usually, the outlet will comprise at least one hole in the housing distal to the aperture. In one embodiment, the catheter includes a nose cone fixed to the distal end of the housing, the nose cone having an axial passage from its proximal end to its distal end, wherein the outlet has a hole at the distal end of the nose cone. The axial passage in the nose cone is configured to receive a movable guidewire, with the hole at the distal end being large enough to receive the guidewire and at the same time allow blood to exit through the hole. At least a portion of the nose cone includes a mesh or porous material to permit bypass flow of blood through the walls of the nose cone.

The perfusion bypass catheter in accordance with this invention provides a method of removing atheroma in a vessel. According to the method of removing atheroma from the inside of a blood vessel in accordance with this invention, the method comprises:

- positioning a distal portion of a catheter body in the vessel, the catheter body having a housing affixed to its distal end, whereby a laterally-facing aperture in the housing is adjacent the atheroma;

axially displacing a cutting blade disposed within the housing across the aperture by means of a drive cable extending through a lumen in the catheter body; and flowing blood through the housing from a proximal side of the blade to a distal side of the blade. Usually, the cutting blade will be rotated or reciprocated by means of a drive motor to facilitate cutting the atheroma. Before, during or after moving the cutting blade, blood is flowed through the housing from a proximal side of the blade to a distal side of the blade to perfuse tissue distal to the housing. According to the various embodiments described above, the blood flows through the housing by slots on the outer surface of the blade, passages through the interior of the blade or through an annular passage between the blade and the housing. Blood is drawn into the housing through openings in the catheter body and/or the housing. In an alternative embodiment, the invention is provided with an impeller to draw blood in and pump blood distally into the housing. After bypassing the blade, the blood exits the housing through openings in the housing or the nose cone.

BRIEF DESCRIPTION OF THE DRAWING

For a further understanding of the objects and advantages of the present invention, reference should be had to the following detailed description, taken in conjunction with the accompanying drawing, in which like parts are given like reference numerals and wherein:

FIG. 2 is a side cross-sectional view of the cutter housing of FIG. 1 with cutter intact.

FIG. 3 is a perspective cross-sectional view through line 3—3 in FIG. 2

FIG. 4 is a transverse cross-sectional view through the line 4—4 in FIG. 2.

FIGS. 5 and 6 are side cross-sectional and end views, respectively, of an alternative embodiment of the cutting blade in the atherectomy catheter of FIG. 1.

FIGS. 7 and 8 are side and end views, respectively, of an alternative embodiment of the cutting blade in the atherectomy catheter of FIG. 1.

FIGS. 9 and 10 are a side partial cut-away view and end view, respectively, of a further embodiment of the drive cable and cutting blade of the atherectomy catheter of FIG. 1.

FIG. 11 is a side cross-sectional view of a further embodiment of the housing (with the cutting blade intact) of the atherectomy catheter of FIG. 1.

FIG. 12 is a perspective cross-sectional view through line 12—12 of FIG. 11.

FIGS. 13 and 14 are side and end views, respectively, of a reciprocating cutting blade in the atherectomy catheter of FIG. 1.

FIG. 15 is a side cross-sectional view of the proximal assembly of the atherectomy catheter of FIG. 1.

FIG. 16 is a side partial cut-away view of a distal portion of the catheter, showing an impeller blade mounted to the drive cable.

FIGS. 17–20 are side views of a further embodiment of the housing and distal portion of the catheter body of the atherectomy catheter of the invention.

FIG. 21 is a side sectional view of another embodiment of the housing and the distal end of the catheter body.

FIG. 22 illustrates an alternative embodiment of a nosecone in accordance with this invention.

FIG. 23 is a perspective view of the interior of the housing showing grooves on the cutter.

DETAILED DESCRIPTION OF THE INVENTION

Figure 1:
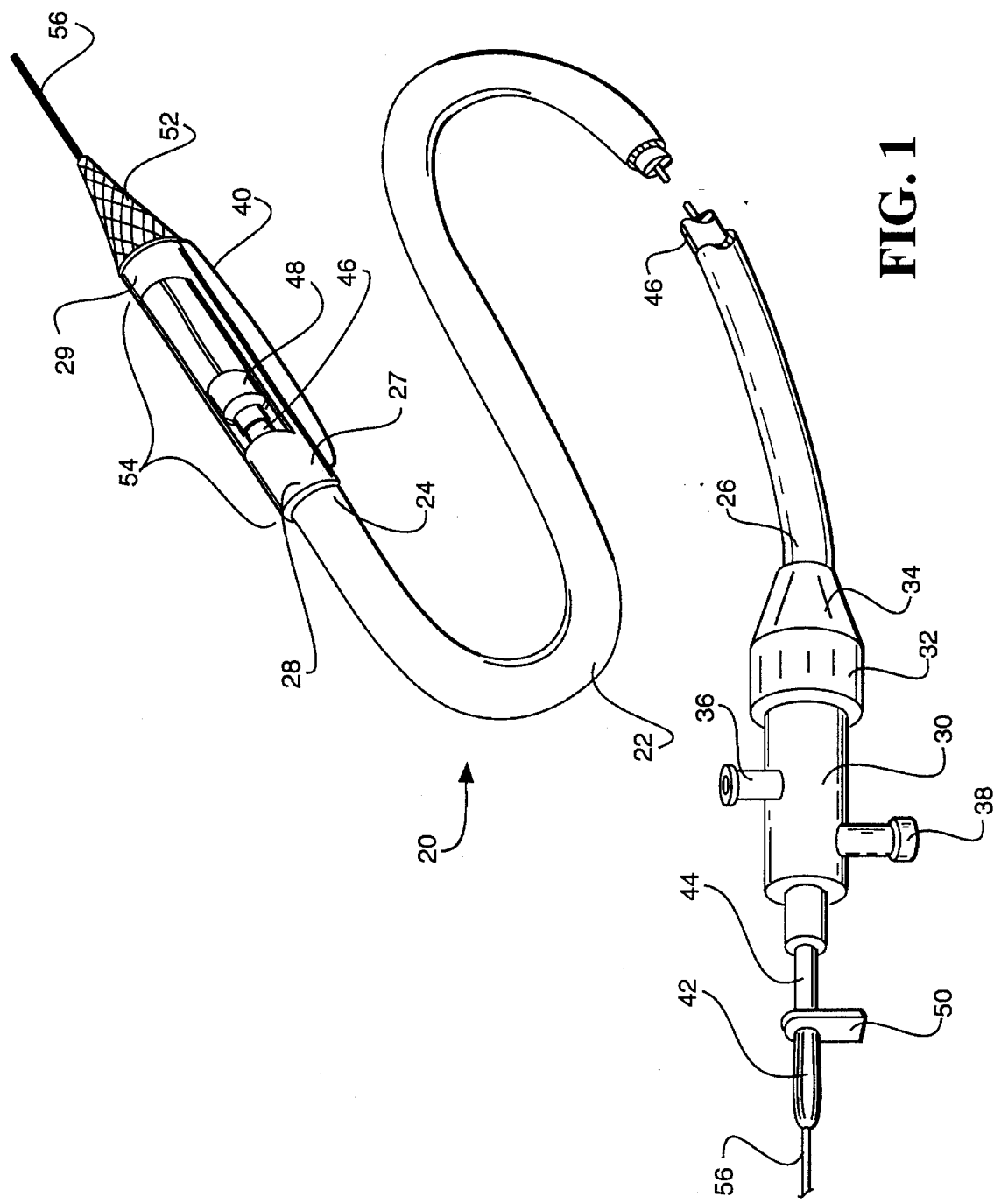
FIG. 1 is a perspective view of an atherectomy catheter constructed in accordance with the principles of the present invention.

The present invention provides improved catheters of the type which include an elongated catheter body with a housing attached toward a distal end, and a work element within the housing. A work element connector extends from the proximal end to the distal end of the catheter body and attaches to the work element. In a preferred embodiment the work element is a cutting blade and the work element connector is a drive cable. The blade can be rotated and/or axially displaced past an aperture formed in a lateral side of the housing. The present invention provides a system for flowing blood through the housing from a proximal side of the work element to a distal side of the work element so as to perfuse tissue downstream from the catheter while the catheter is positioned in the vessel.

The perfusion structure in accordance with the present invention is useful with a wide variety of catheters having virtually any type of work element such as cutting blades for performing atherectomy procedures, heated elements for performing thermal ablation, electrodes for performing electrosurgical cutting and cauterization, abrasive elements for performing mechanical ablation, optical waveguides for performing laser ablation, ultrasonic transducers for imaging and ablation and the like. It is to be appreciated that each type of work element has a work element connector that corresponds functionally to the work element, such as a drive cable, electrical wiring, fiber optics and the like.

The perfusion structure in accordance with the present invention is particularly useful in atherectomy applications where a rotating or reciprocating cutting blade is simultaneously rotated or reciprocated and axially advanced past a side aperture in a cutter housing in a known manner. Such atherectomy devices and procedures are described in U.S. Pat. Nos. 4,669,469; 4,926,858; 4,979,951; 5,047,040; 5,084,010;

U.S. Pat. No. Re. 33,569 and co-pending application Ser. No. 08/224,169 entitled "Directional Atherectomy Device with Flexible Cutter", Attorney Docket No. DEVI1467, the full disclosures of which are incorporated herein by reference.

Referring now to the drawings, a number of embodiments of catheters employing blood bypass systems constructed in accordance with the principles of the present invention are described.

FIG. 1 illustrates an atherectomy catheter 20 that includes a moveable guidewire 56, a nose cone 52, a cutter housing 27 (generically referred to as "work element housing") with an elongated aperture or window 54, a flexible catheter body 22 with a drive cable 46 (generically referred to as "work element connector") therein, and a proximal assembly 30. The work element housing 27 receives the drive cable 46 and a work element or cutter blade 48.

The atherectomy catheter 20 is introduced over the movable guidewire 56 which extends through a guidewire lumen in catheter body 22. The guidewire parallels the longitudinal axis of the catheter 20. The guidewire lumen is disposed centrally within drive cable 46, drive shaft 44 and spline 42, as illustrated.

The catheter body 22 has a proximal end 26. A rotator assembly 32 connects proximal end 26 of the catheter body 22 to proximal assembly 30 and facilitates rotation of the catheter body 22 relative to the proximal assembly 30. Transition element 34 provides stress relief in the connection between catheter body 22 and proximal assembly 30. A spline 42 adapted for connection to a motor drive unit (MDU) (such as that disclosed in U.S. Pat. No. 4,771,774, the disclosure of which is incorporated herein by reference) is secured to a drive shaft 44 which in turn is connected to a drive cable 46 which extends through an axial lumen the entire length of the catheter body 22.

The catheter body 22 also has a distal end 24. The cutting blade housing 27 has a proximal end 28 and a distal end 29. The proximal end 28 is attached to the distal end 24 of the catheter body 22.

A cutting blade 48 is attached to the distal end of drive cable 46 within the housing 27. The cutter housing 27 further includes an elongated side aperture or window 54 through which a portion of blade 48 is exposed. Stenotic material from the blood vessel which is positioned through aperture 54 is severed by axial translation of the cutter 48 across the aperture. An axial advance lever 50 is mounted to drive shaft 44 and rotationally decoupled therefrom so as to permit manual translation of drive cable 46 and cutter 48 in the axial direction.

The housing 27 is connected at its distal end 29 to a nose cone assembly 52. Alternatively, the nose cone 52 is a spring coil, mesh, polymeric tube or other flexible structure.

An optional balloon inflation system is also shown. A luer fitting 36 on proximal assembly 30 connects to a balloon inflation lumen (not shown) in catheter body 22 to facilitate inflation of a balloon 40 on the cutter housing 27. The balloon 40, mounted to cutter housing 27 opposite aperture 54, is inflated to urge the housing 27 against the stenotic region.

An optional flush or perfusion system is also shown. Connector or flush port 38 on the proximal assembly 30 connects to a passage or lumen (not shown) within catheter body 22 to permit connection of a perfusion or aspiration source.

FIGS. 2 and 4 illustrate the cutter housing 27, the distal end of the catheter body 22, and the nose cone 52. FIG. 4 is a end view through line 4-4 of FIG. 2. The illustrations show the longitudinal axis 41 of the cutter housing 48, the cutter housing aperture 54, a cutting blade 48, an open interior 60 within which the cutter 48 is slidably disposed, openings 70 and an annular lumen 72 of the catheter body 22, and a drive cable 46.

The cutting blade 48 is supported and guided by the interior surface 2 of housing 27 opposite the window 54. The cutting blade 48 is designed to slide in close tolerance with parting surface 64 on the distal side of the aperture 54 to part off stenotic material as the cutter 48 slides forward. The cutting blade 48 is cylindrical and has an open interior which broadens outward toward its distal end defining a circular cutting edge 66 about the periphery of the distal end of the cutting blade 48.

In combination with FIGS. 2 and 4, FIG. 3 illustrate an embodiment of the cutter 48 and housing 27. FIG. 3 is a perspective view through line 3—3 of FIG. 2 showing passages or slots 68 in the cutting blade 48.

In this embodiment, the cutting blade 48 has one or more slots 68 on its outer surface extending from a proximal side to a distal side of the blade. The slots 68 provide a passage between the cutter 48 and the housing 27 for bypass flow of blood. The blood flows into the housing through openings 70 in the catheter body 22. Additionally, openings can be provided in the housing 27 proximal to the aperture 54. The openings 70 are in communication with a lumen 72 between the drive cable 46 and the catheter body 22. The blood flows through the openings 70 into the annular lumen 72 and distally to the cutter 48. The blood then bypasses the cutter 48 through the slots 68, and exits the housing 27 through aperture 54, or through the outlet openings 74 in the housing distal to the aperture 54. Blood also exits housing 27 through the nose cone 52, as described more fully below.

FIGS. 5 and 6 illustrate an embodiment of the cutter 48 with internal passages or tunnels 76. One or more tunnels 76 extend from the proximal side to the distal side of the cutter 48 and the tunnels 76 have a distal opening within the hollow interior 78 of the cutter 48. The internal tunnels 76 provide for the flow of blood from the proximal to the distal side of the cutter 48.

FIGS. 7 and 8 illustrate another embodiment of the cutter 48 with a helical slot or groove 86 disposed in the outer surface of cutter 48. The helical groove 86 spirally encircles the cutter 48 in an orientation that causes blood to flow through the groove 86 as the blade 48 rotates. During rotation of the cutter 48 blood is impelled in a generally distal direction, actively assisting flow through the housing 27 to bypass the cutter 48.

FIGS. 9 and 10 illustrate an embodiment of the drive cable 46 with an axial passage 88 and inlet holes 90, and the cutter 48 with a central passage 92. The inlet holes 90 are disposed in the side wall of the drive cable 46 in communication with the passage 88. The cutter 48 has a central passage or bore 92 extending axially therethrough. The blood flows into the annular lumen 72 of the catheter body 22 through the openings in the catheter body 70 (shown in FIG. 2). The blood then flows through the inlet holes 90 into the passage 88 within the drive cable 46 and distally through the bore 92 in the cutter 48. Blood then exits the housing through the aperture 54, the outlet openings 74 or the nose cone 52 (FIG. 2). The axial passage is usually configured to receive the movable guidewire 56 (illustrated in FIG. 1 ).

FIGS. 11 and 12 illustrate an additional embodiment of the cutter 48 and housing 27 with a guide shaft 96. The cutter 48 is undersized with respect to the interior 60 of the housing 27 so as to permit bypass flow of the blood through an annular space 94 between the periphery of the cutter 48 and the interior wall 62 of the housing. In a preferred embodiment, the blade 48 will have a cross-sectional area which is in the range of 60% to 99.5% of the cross-sectional area of the interior 60 of the housing 27, preferably in the range of 75% to 98%. It is important that the blade 48 is supported and guided within the housing 27 in such a way that the cutting edge 66 at the periphery of the blade engages stenotic material in the aperture 54, and slides closely under parting surface 64 to part off tissue at the distal side of the aperture. To provide such support and guidance, a guide shaft 96 is mounted in the housing 27 and extends through an axial bore 98 in the blade 48. The guide shaft 96 is attached at its distal end to the distal tip 100 of the nose cone 52, typically being secured by a ring. The guide shaft 96 can be either rigid or flexible, depending upon the nature of the housing 27, typically being flexible when located in a flexible housing. In one embodiment, the guide shaft 96 is formed from a super-elastic alloy such as nickel-titanium alloy, e.g., Nitinol®, available commercially from Advanced Cardiovascular systems. In one embodiment the guide shaft 96 extends through the axial passage 102 in the drive cable 46 to the proximal end of the catheter body 22. Alternatively, the guide shaft 96 is cantilevered from its distal end terminating within the housing 27 and unattached to a support structure. In this way, the cutter 48 is translated axially over the guide shaft 96, which maintains the position of the cutter within the aperture 54 and ensures a close, sliding fit against parting surface 64. The guide shaft 96 is also provided with an axial guidewire lumen 104 for receiving a movable guidewire.

FIGS. 13 and 14 illustrate an embodiment of the cutter 48 and guide shaft 96. The cutter 48 is disposed over the guide shaft 96, which extends through an axial bore 106 in the cutter 48. The cutter 48 is configured to rotationally reciprocate or oscillate about the guide shaft 96, rather than having complete rotational motion as in previous embodiments. The cutting portion 108 of the cutter 48 is located in an exposed position in the aperture 54 (FIG. 11) and rotationally oscillates therein, while a portion of the cutter opposite the cutting portion 108 is slotted or open, so as to leave a portion of interior 60 (FIG. 11) of the housing substantially unobstructed. In this way, blood flows into the interior of the housing and past the cutter 48 while the cutter reciprocates back and forth within the aperture 54.

A variety of structures can be used for supporting and guiding the cutter 48 in the embodiments illustrated in FIGS. 11, 12, 13 and 14. Various types of work element guide systems for atherectomy catheters are described in co-pending application Ser. No. 08/363,142, Attorney Docket No. DEVI1456, entitled "Universal Catheter with Interchangeable Work Element".

FIG. 15 illustrates an embodiment of the proximal assembly 30, shown in relation to the rest of the atherectomy catheter in FIG. 1. The proximal assembly 30 comprises a connector 38 with a perfusion port 80 in communication with an axial lumen 82 extending through the catheter body 22 extending to its distal end 24 (FIG. 1). An O-ring 84 seals the annular lumen 82 proximal to the perfusion port 80. Operationally, blood is introduced into the perfusion port 80 and flows distally through the lumen 82 into the housing 27 at the distal end 24 of the catheter body 22 (FIG. 1). The blood then bypasses the cutter 48 in the manner described above with reference to FIGS. 2–14.

FIG. 16 illustrates an additional embodiment of the cutter 48, housing 27, catheter body 22, and drive cable 46. In this embodiment an impeller blade 110 is mounted to the drive cable 46 within the axial passage 112 at the distal end of the catheter body 22. Alternatively, the impeller blade 110 is helical as shown, or comprises radially extending fins or propeller blades. Openings 114 are provided in the sidewall of the catheter body 22 near the impeller blade 110. Rotation of the drive cable 46 rotates the impeller blade 110, actively drawing blood through the openings 114 and pumping blood distally into the interior 60 of the housing 27. The blood then bypasses the cutter 48 by means of slots 68 on the outer surface of the blade, as described above, or by one of the various other bypass means previously described. In a preferred embodiment, the helical blade 110 is made of a semi-flexible material such as butyl rubber or other organic polymer. An O-ring or other seal (not shown) is also provided within the axial passage 112 proximal to the impeller blade 110 and the side holes 114 to seal off the proximal portion of the axial passage, improving pumping efficiency.

Various embodiments of the housing 27, nose cone 52 and cutter 48 with the helical groove 86 are illustrated in FIGS. 17 through 20. FIG. 17 illustrates a housing 27 incorporating a plurality of openings or ports 116 in communication with the interior of the housing 27 distal, adjacent and proximal to the aperture 54. When the cutter 48 is rotated, the helical groove 86 draws blood through the ports 116 proximal to the cutter 48 and impels blood distally through the housing 27, from which blood exits through the ports 116 distal to the cutter 48 through the aperture 54, or through the nose cone 52.

FIG. 18 illustrates ports 116 only on the proximal side of the aperture 54 for purposes of drawing blood into the interior of the housing. The helical groove 86 on the cutter 48 pumps blood distally through the housing, from which blood exits through the aperture 54, or through the openings or outlet ports 118 in the nose cone 52. The nose cone 52 is also provided with a distal port 130 at or about its apex through which blood exits the housing.

FIG. 19 illustrates transverse slots 120 proximal and distal to the aperture 54 in the housing 27. Such slots are ordinarily used when a flexible housing is desirable, since the slots increase the bendability of the housing 27. Blood is drawn in through the transverse slots 120 proximal to the cutter 48 by rotation of cutter 48. Blood is impelled through the helical groove 86 in the cutter, and exits the housing through the aperture 54, through the transverse slots 120 distal to the cutter 48, or through the nose cone 52.

FIG. 20 illustrates a transition tube 122 attached between the distal end 24 of the catheter body 22 and the proximal end 28 of the housing 27. The transition tube 122 is a flexible material, for example, a super-elastic alloy such as Nitinol®, providing a flexible connection between the catheter body 22 and the housing 27. The transition tube 122 preferably contains inlet ports 124 to provide a passage for inflow of blood into the housing 27. This eliminates the need for forming openings in the housing 27 or the catheter body 22 which, in some cases, is desirable to improve manufacturability or to maintain rigidity.

FIG. 20 further illustrates an embodiment of the nose cone 52, wherein a distal portion 126 of the nose cone comprises a conical coil spring, which is metallic and/or polymeric. A proximal portion 128 of the nose cone comprises a mesh structure to permit outflow of blood from the housing 27. Of course, such a mesh portion could be incorporated in the nose cones of any of the previous embodiments.

In any of the above embodiments, all or a portion of the nose cone 52 can be composed of a mesh or porous material through which blood exits the housing. The mesh or porous material can be metallic or polymeric and provides flexibility to the nose cone. Where less flexibility is desirable in the nose cone, a rigid polymer or metal structure is used, with distal and/or side ports in the nose cone to permit outflow of blood from the housing.

FIG. 21 illustrates, an embodiment of the nose cone 52, housing 27, cutter 48 and a distal portion of the catheter body 22 with an enlarged diameter so as to define a receiving space 130 into which the cutter 48 is retractable from the housing 27. Openings 132 are formed in the housing 27 or the catheter body 22, such that the cutter 48 is retracted proximal to the side holes 132. Blood flows into the housing 27 through the side holes 132 and forward through the housing 27, exiting either through the aperture 54, the outlet ports 134 or the port 130 at the distal end of the nose cone. Atherectomy catheters designed to allow retraction of the work element from the housing are also described in co-pending application Ser. No. 08/363,142, Attorney Docket No. DEVI1456, entitled "Universal Catheter with Interchangeable Work Element".

FIG. 22 illustrates an embodiment of a nose cone, generally indicated by the numeral 52. The nose cone 52 includes a nose cone housing 202 and a mesh insert 204. The mesh insert is sized and shaped for compatible fit within the nose cone housing 202. The nose cone housing 202 and mesh 204 are preferably frusto conical in shape. In this embodiment, the nose cone mesh 204 allows a lumen 206 to be formed between the mesh and the nose cone housing 202. Additionally, another lumen 208 is formed by the mesh 204, itself. As stenotic material is deposited in the nose cone 52, blood perfuses to the tissue through the nose cone 52 via either the first lumen 206 or the second lumen 208. Thus, if the lumen's main chamber 208 is filled by stenotic material, the first lumen 206 will still be available for perfusion.

FIG. 23 illustrates an embodiment of the cutter housing 27. The housing 27 has axial grooves 222 on its inner surface 60 which allow blood to flow annularly past the cutter 48. In this illustration the grooves 222 are longitudinal. Alternatively, the grooves 222 can be helical or any other geometric configuration within the spirit and scope of this invention. As shown, the profile shape of the grooves 222 are shown as being generally rectangular, but a variety of different geometric configurations, such as semi-circular, are also within the spirit and scope of this invention. Of course, a cutter housing 27 with grooves 222 can be used in conjunction with a cutter blade 48 with slots 68 (FIG. 3) or with any of the cutter blade embodiments described herein.

Where stenosis has caused narrowing of the vessel lumen, catheters and housings presently in use occlude much if not all of the remaining open portion of the vessel lumen. For this reason, the catheter of the invention provides a perfusion system whereby blood is flowed through the housing 27 from a proximal side of the blade 48 to a distal side, thereby perfusing tissue downstream of the catheter 20.

The atherectomy catheter 20 of the invention is particularly advantageous in that it remains positioned in a vessel for extended periods, either for purposes of training inexperienced users, or for atherectomy treatments of longer duration, without risk of creating an ischemic reaction in the patient. The catheter provides bypass flow of blood both when the cutter 48 is in a stationary position, as well as when the cutter is rotating. Thus, tissue downstream of the catheter 20 is perfused while the catheter is being positioned in the vessel, while the cutter is being rotated or oscillated to remove stenotic material and while the cutter is idle with the catheter remaining positioned in the vessel.

According to the methods of using the present invention, the atherectomy catheter 20 (FIG. 1) is positioned in a blood vessel, such as an artery, so that the housing 27 is near a treatment site. Preferably, a movable guidewire 56 previously inserted within the vessel is used to facilitate positioning the catheter 20 in the vessel. The catheter is positioned such that the aperture 54 is adjacent the stenotic material such that the stenotic material protrudes through the aperture 54 into the open interior 60 of the housing 27. If a balloon 40 (FIG. 1) is provided, it is inflated so as to urge the housing 27 against the wall of the vessel and to position the stenotic material within the aperture 54.

The catheter of the invention provides a blood bypass system whereby blood flows through the housing 27 and distal to the device so as to perfuse downstream tissue. Using the embodiment illustrated in FIG. 17 for example, blood will enter the housing through the openings 116 proximal to the cutter 48, and flows distally through the helical groove 86. As the cutter 48 rotates, the blood is impelled downstream to increase flow. Blood will then exit the housing 27 through the openings 116 distal to the cutter, or through the nose cone 52.

The embodiment illustrated in FIG. 16 provides positive pumping action by the helical impeller blade 110 which draws blood through the openings 114 and pumps it distally into the interior 60 of the housing. In a further embodiment, blood is introduced through a flush port in proximal assembly 30 (FIG. 1) and moved distally through the axial passage in the catheter body into the housing 27. The blood then bypasses the blade 48 through the slots 68.

In an alternative embodiment illustrated in FIG. 21, the cutter 48 is retracted into a receiving space 130 at the distal end of the catheter body 22 permitting less resistance to blood flowing into the housing through openings 132, whereupon it exits the housing through the aperture 54, the outlet openings 134 or through the distal opening 130 in the nose cone 52.

Removal of stenotic material is accomplished by translating the cutter 48 axially across the aperture 54, with the blade 48 rotating, or rotationally reciprocating as illustrated in FIG. 13, typically by means of a drive motor coupled to spline 42 at the proximal end of the drive cable 46 (FIG. 1). As the blade is advanced forward across the aperture, stenotic material is severed and captured within the open interior of the blade. The stenotic material is stored within cutter 48, or pushed distally into the nose cone 52, where tissue is retained.

The elongated catheter body 22 of the present invention typically comprises a flexible tube which is similar in construction to a wide variety of intravascular catheters, the type of which are well known in the art. In a preferred embodiment the flexible tube has a proximal end and a distal end and at least one lumen extending therebetween. The tube is formed by extrusion of an organic polymer, typically a thermoplastic, such as nylon, polyurethane, polyethylene terephthalate (PET), polyvinylchloride (PVC), polyethylene and the like. The tubes are reinforced or unreinforced, usually being reinforced by a metal braid which is laminated with a polymeric material. Use of the metal braid reinforcement layer is desirable since it facilitates torquing and positioning of the cutter housing. The catheter body 22 typically has a length from about 40 cm. to about 200 cm., with shorter catheters in the range from about 40 cm. to 120 cm. being used for peripheral applications and longer catheters in the range from about 100 cm. to 200 cm. being used for coronary applications. The diameters of the catheter bodies also vary, with small diameter catheters in the range from about 3French (F; 1F=0.33 mm) to 8F used for coronary applications and a diameter from 3F to 11F for peripheral applications.

The cutter housing 27 usually has a cylindrical structure with an elongated aperture 54 along one side thereof. The housing 27 is rigid or flexible, typically being formed from a metal, such as surgical stainless steel or an organic polymer, such as nylon, polyurethane. In this context rigid means that the housing has a generally continuous construction, usually composed of a metal or rigid plastic, including the side aperture, but free from other spacings or voids intended to enhance bendability. In this context flexible means that the housing is formed from a resilient material, such as elastic, or if formed from metal, it includes spacings or voids to facilitate bending. The construction of particular flexible housings are illustrated in U.S. Pat. No. 4,781,186 and co-pending application Ser. No. 07/726,626, the disclosures of which are incorporated herein by reference.

The length of the cutter housing 27 depend primarily on the desired length of stenotic material to be severed, with the limitation that longer housings are more difficult to manipulate through the vascular system. Typically, the length of the housing 27 is from 5 mm. to 40 mm. For coronary applications, the housing length is generally short, usually from about 8 mm to about 17 mm. The housing diameter generally corresponds to the diameter of the flexible tube, i.e., usually from about 3F to about 11F.

The cutter aperture 54 of the housing 27 typically extends over at least half of the housing length, more typically it extends over at least three-quarters of the housing length. It is desirable to maximize the length of the housing 27 in order to increase the amount of the stenotic material which can be removed in a single pass of the cutting blade 48.

In an embodiment, the cutting element 48 is a cup-shaped cutting blade which is rotated (or rotationally oscillated or reciprocated) and axially advanced to sever the atheroma and move the atheroma toward the distal end of the housing 27. Such cutting blades are discussed in U.S. Pat. No. 4,979,951 and reissued U.S. Pat. No. Re. 33,569, the disclosures of which are incorporated herein by reference.

In an embodiment, the distal portion 24 of the catheter body 22 or the proximal portion 28 of the housing 27 receives all or a portion of the cutting blade 48, permitting passages provided in the catheter body 22 and/or the housing 27 to be repositioned distal to the cutting blade 48, thereby permitting blood to flow with less resistance into the housing 27 on a distal side of the blade 48. Catheters designed to permit the cutting blade to be withdrawn from the housing into the catheter body are described in co-pending application Ser. No. 08/363,142, Attorney Docket No. DEVI1456, entitled "Universal Catheter with Interchangeable Work Element", the complete disclosure of which is incorporated herein by reference.

While the foregoing detailed description has described a preferred embodiment of the catheter with perfusion system in accordance with this invention, it is to be understood that the above description is illustrative only and not limiting of the disclosed invention. Particularly, the specific details of the catheter body can differ from those illustrated and described so long as tissue downstream of the catheter is perfused while the catheter is in place in the blood vessel. Furthermore, the manner of catheterization can differ from that disclosed so long as the tissue downstream of the catheter is perfused while the catheter is in place in the blood vessel. Thus the invention is to be limited only by the claims set forth below.

What is claimed is:

1. An atherectomy catheter comprising:

a catheter body having a distal end, a proximal end and a lumen therebetween;

a housing having a longitudinal axis, a hollow interior, a proximal end affixed to the distal end of the catheter body, a distal end, a perfusion port entry, a perfusion port exit, and an aperture on a lateral side of the housing;

a work element disposed in the housing;

a work element connector with a proximal end and a distal end, the connector disposed in the catheter body with the distal end affixed to the work element, the perfusion port entry being proximal the work element, the perfusion port exit being distal the work element; and the housing defines at least one passage, the passage being in fluid communication with each perfusion port to facilitate perfusion of fluid through the housing and past the work element.

2. A catheter as set forth in claim 1, wherein the work element comprises a cutting blade movable in an axial direction, and wherein the affector connector comprises an axially translatable drive cable.

3. A catheter as set forth in claim 2, wherein the blade is rotatable, having a hollow interior, an open distal end, and a proximal end, the proximal end of the blade connected to the drive cable.

4. A catheter as set forth in claim 3, wherein the perfusion port exit includes a nose cone fixed to the distal end of the housing, the nose cone having hollow interior.

5. A catheter as set forth in claim 4, wherein the nose cone contains a mesh insert.

6. A catheter as set forth in claim 4, wherein the drive cable is coupled to a drive motor.

7. An atherectomy catheter as set forth in claim 4 wherein at least one passage is a groove on the interior surface of the housing.

8. A catheter as set forth in claim 4, wherein at least one passage is a slot in an outer surface of the cutting blade extending from the proximal end to the distal end thereof.

9. A catheter as set forth in claim 8, wherein the slot is parallel to the longitudinal axis.

10. A catheter as set forth in claim 8, wherein the slot is helical.

11. A catheter as set forth in claim 10, wherein the helical slot is configured to impel blood distally as the blade rotates.

12. A catheter as set forth in claim 8, wherein the blade is rotationally reciprocal and the slot is disposed within the portion of the blade that remains in contact with an interior wall of the housing.

13. A catheter as set forth in claim 4, wherein at least one passage is a tunnel extending through the blade from the proximal end to the distal end.

14. A catheter as set forth in claim 4, wherein an annular passage exists between the cutting blade and the housing.

15. A catheter as set forth in claim 14, wherein the cutting blade has a cross-sectional area in the range of 75% to 98% of the cross-sectional area of the interior of the housing.

16. A catheter as set forth in claim 4, wherein the perfusion port entry includes at least one opening in the catheter body, proximal to the aperture of the housing to facilitate fluid to enter the housing.

17. A catheter as set forth in claim 4, further comprising at least one opening in the catheter body or the housing, proximal to the aperture of the housing permitting fluid to flow in or out of the housing.

18. A catheter as set forth in claim 17, wherein the drive cable has an axial passage and at least one inlet hole near its distal end in communication with the axial passage, and the blade has an outlet hole on a distal side that is in communication with the axial passage, wherein fluid is permitted to flow through the axial passage.

19. A catheter as set forth in claim 17, wherein the distal end of the catheter body comprises a receiving space configured to receive at least a portion of the cutting blade, whereby the cutting blade is retractable proximal to the opening.

20. A catheter as set forth in claim 17, wherein the perfusion port exit includes at least one opening in the housing distal to the aperture of the housing to facilitate perfusion of fluid in or out of the housing.

21. A catheter as set forth in claim 17, further comprising an impeller blade fixed to the drive cable.

22. A catheter as set forth in claim 21, wherein the impeller blade is helical.

23. An atherectomy catheter for insertion into a blood vessel, comprising:

a catheter body having a distal end, a proximal end and a lumen therebetween;

a housing attached to the distal end of the catheter body, the housing has a perfusion port entry, a perfusion port exit, and a lateral side which defines an aperture for receiving stenotic material;

a work element moveably disposed in the housing, the work element defines a portion of at least one passage, the passage being in fluid communication between the perfusion port entry and the perfusion port exit to facilitate perfusion of fluid through the housing and past the work element; and a drive cable, being disposed in the lumen of the catheter body, the drive cable has one end affixed to the work element for moving the work element, whereby, when the catheter device inserts into a blood vessel, blood enters the housing through the perfusion port entry, flows through the passage, past the work element, and exits the housing past the work element through the perfusion port exit.

24. A device as set forth in claim 23, wherein the cable defines a portion of the passage, the cable includes an impeller blade to facilitate perfusion.

25. A device as set forth in claim 23, wherein the catheter body defines a portion of the perfusion port entry.

26. A device as set forth in claim 23, wherein the catheter has a nosecone, the perfusion port entry includes an aperture for drawing blood into the housing and the perfusion port exit includes outlet ports defined on the nosecone for facilitating perfusion of fluid.

27. A device as set forth in claim 23, wherein the perfusion port exit includes a nosecone attached to the housing, the nosecone includes a mesh insert to facilitate the perfusion of blood from the housing.

28. A device as set forth in claim 23, wherein the work element has a helical groove to define a portion of the passage.

29. A device as set forth in claim 23, wherein the work element connector has a central passage and holes, the work element is a cutter having a bore to define a portion of the passage of the housing.

30. A device as set forth in claim 23, wherein the passage of the work element includes slots.

31. A device as set forth in claim 23, wherein the passage of the work element includes tunnels.

32. A device as set forth in claim 23, wherein the housing includes a guide shaft.

* * * * *